United States Patent [19]

Schittenhelm

[11] Patent Number: 4,914,588

[45] Date of Patent: Apr. 3, 1990

[54] COMPUTER TOMOGRAPHY APPARATUS FOR GENERATING AN IMAGE OF A PORTION OF A SECTIONAL SLICE OF A SUBJECT FOR USE WITH A LITHOTRIPSY APPARATUS

[75] Inventor: Rudolf Schittenhelm, Erlangen, Fed. Rep. of Germany

[73] Assignee: Siemens Aktiengesellschaft, Berlin and Munich, Fed. Rep. of Germany

[21] Appl. No.: 242,222

[22] Filed: Sep. 9, 1988

[30] Foreign Application Priority Data

Oct. 8, 1987 [DE] Fed. Rep. of Germany ....... 8713524

[51] Int. Cl.⁴ .................. A61B 6/03; A61B 17/22; G01T 1/29
[52] U.S. Cl. .................. 364/413.14; 364/413.15; 364/413.26; 378/15; 378/19
[58] Field of Search ............ 378/15, 19; 128/328; 364/413.14, 413.18, 413.26

[56] References Cited

U.S. PATENT DOCUMENTS

| 4,118,631 | 10/1978 | Froggatt | 378/65 |
| 4,176,279 | 11/1979 | Schwierz et al. | 378/4 |
| 4,550,371 | 10/1985 | Glover et al. | 364/413.2 X |
| 4,589,415 | 5/1986 | Haaga | 128/328 |
| 4,662,379 | 5/1987 | Macovski | 378/15 X |
| 4,705,026 | 11/1987 | Chaussy et al. | 128/24 A |
| 4,731,807 | 3/1988 | Plessis et al. | 378/15 G |
| 4,769,828 | 9/1988 | LeMay | 378/15 X |
| 4,783,795 | 11/1988 | Yahata | 378/15 X |
| 4,803,995 | 2/1989 | Ishida et al. | 128/328 X |
| 4,819,257 | 4/1989 | Grasser et al. | 128/328 X |

Primary Examiner—Clark A. Jablon

[57] ABSTRACT

A third generation computer tomography apparatus has a radiation detector which is so narrow that the image constructed by the computer represents only a portion of a cross-sectional slice of an examination subject. The apparatus is useful for examining smaller body regions, such as to locate a calculus to be disintegrated. The tomography apparatus can be combined with a lithotripsy apparatus, including a shock wave generator, for this purpose.

8 Claims, 3 Drawing Sheets

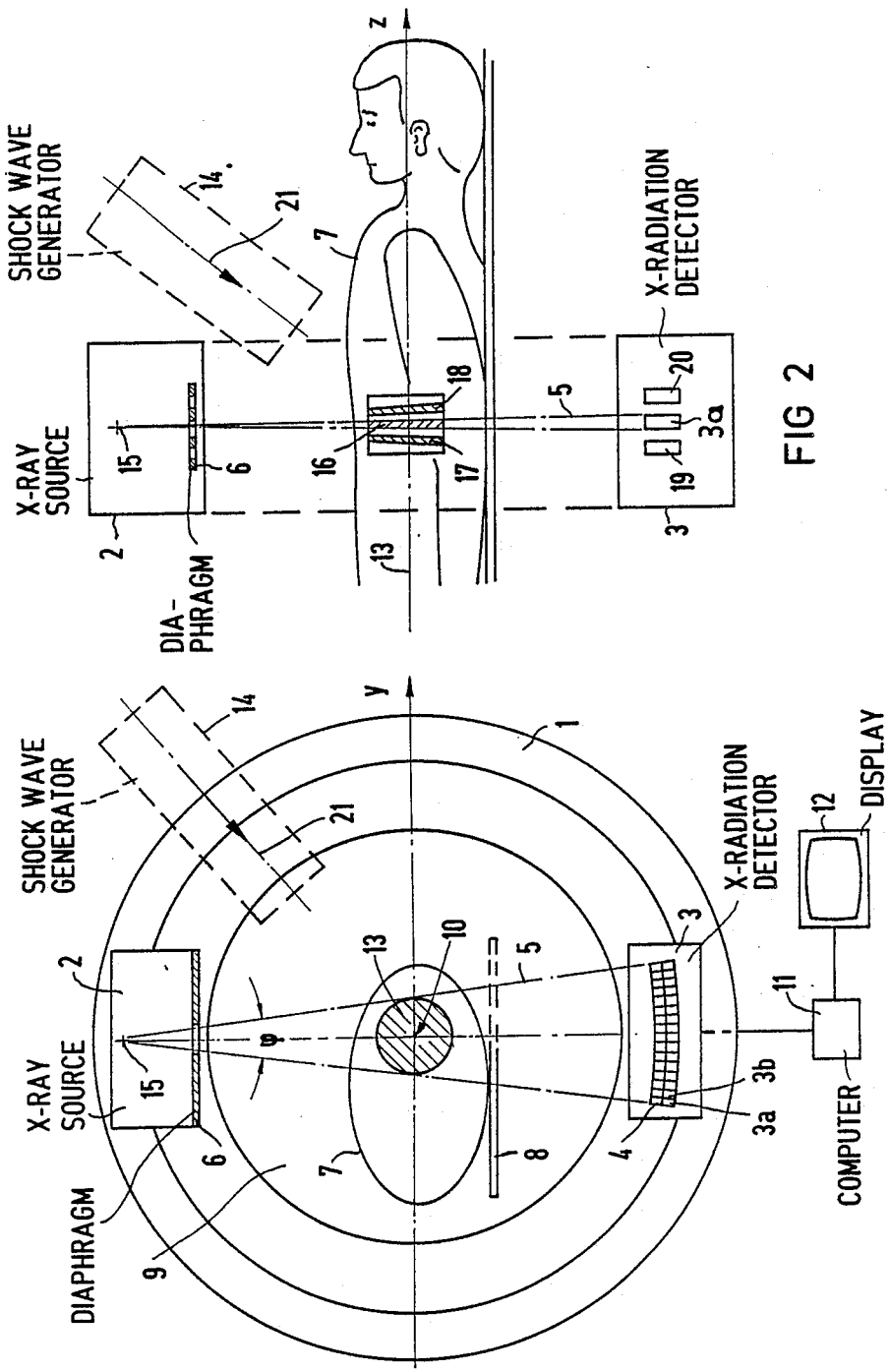

COMPUTER TOMOGRAPHY APPARATUS FOR GENERATING AN IMAGE OF A PORTION OF A SECTIONAL SLICE OF A SUBJECT FOR USE WITH A LITHOTRIPSY APPARATUS

BACKGROUND OF THE INVENTION

1. Field of the Invention

The present invention is directed to a third generation computer tomography apparatus, and in particular to such an apparatus suitable for use in combination with extracorporeal lithotripsy equipment.

2. Description of the Prior Art

Computer tomography devices are known in the art which include an x-ray source which generates a fan-shaped radiation beam and a radiation detector formed by a row of detector elements. The measuring unit is seated to be rotatable around an axis which extends through a measuring field in which a patient on a patient support is disposed, so that the patient is irradiated from different directions. A computer is connected to the radiation detector and constructs an image of the transirradiated slice of the patient from the output signals of the detectors. This type of computer tomography apparatus is known in the art as a "third generation" computer tomography apparatus.

In computer tomography devices of this type, a patient aperture is disposed in the center of the measuring unit, through which a patient support extends. The radiation detector in such conventional devices has a width such that the measuring field covers the entire patient cross-section. To achieve good resolution, a relatively large number of detector elements, for example 512 detector elements is required. Accordingly such a computer tomography apparatus represents a relatively expensive medical diagnostic instrument.

SUMMARY OF THE INVENTION

It is an object of the present invention to provide a third generation computer tomography apparatus having a simplified and less expensive structure than conventional units of that type.

It is a further object of the present invention to provide such a computer tomography apparatus which can be used in combination with a lithotripsy apparatus.

The above objects are achieved in accordance with the principles of the present invention in a computer tomography apparatus wherein the measuring field is significantly smaller than the measuring field of conventional third generation tomography devices, and extends through only a portion of a cross-sectional slice of the examination subject. Generating an image of such a relatively small region of the patient is sufficient for certain purposes, for example, for locating calculi in the body of the patient for subsequent disintegration with a lithotripsy device. The computer tomography apparatus disclosed herein has a radiation detector which is so narrow that the image constructed by the computer from the output signals of the detector constitutes only the portion of interest of the cross-section of an average patient.

The computer tomography apparatus disclosed herein is particularly suited for use in combination with a lithotripsy apparatus to locate calculi to be disintegrated, because a relatively small measuring field is sufficient for this purpose. Certain types of calculi, for example gallstones, can be portrayed significantly better in a computer tomograph than in standard x-ray shadow images. Monitoring the success of the lithotripsy treatment is also more easily seen in a computer tomograph, because the small dimensions of the calculus fragments after disintegration make the fragments difficult to discern in x-ray shadow images and in ultrasound images. Because of the reduced number of detector elements in the radiation detector, and the smaller fan angle of the x-ray beam, the computer tomography device disclosed herein makes use of the device in this manner economically reasonable.

DESCRIPTION OF THE DRAWINGS

FIG. 1 is an end elevational view of a computer tomography apparatus constructed in accordance with the principles of the present invention.

FIG. 2 is a side view of the computer tomography apparatus shown in FIG. 1.

DESCRIPTION OF THE PREFERRED EMBODIMENTS

Figure 3:
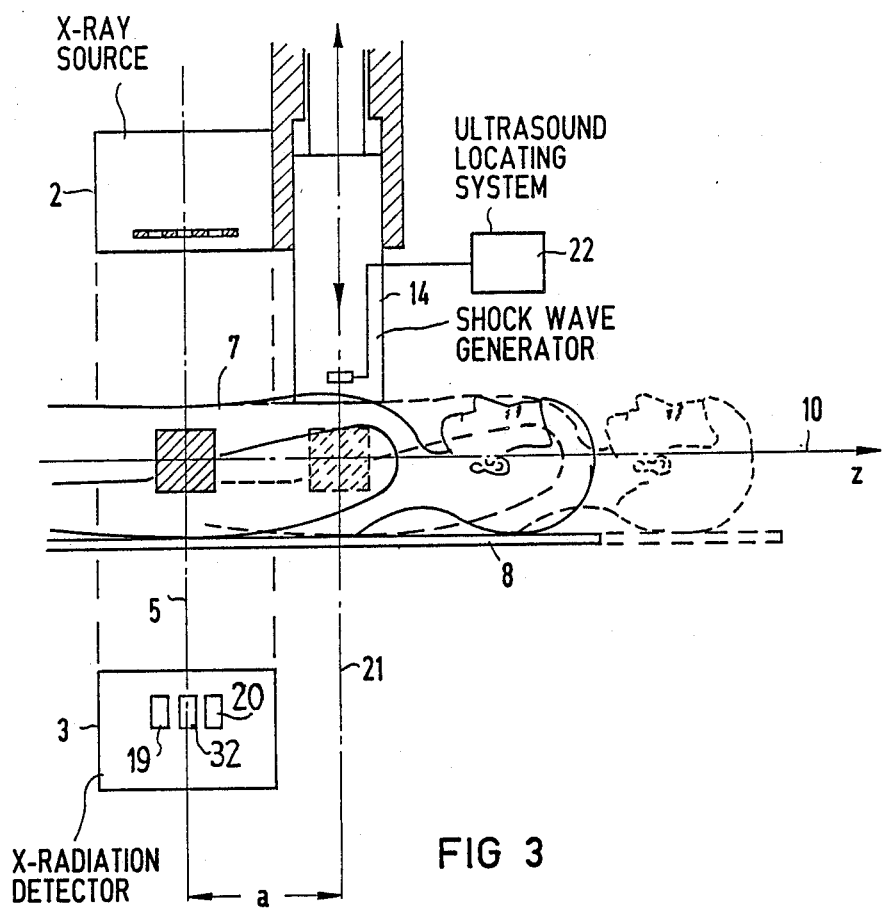
FIGS. 3 and 4 are side views of the relevant portions of a computer tomography apparatus constructed in accordance with the principles of the present invention combined with a lithotripsy apparatus.

The computer tomography apparatus shown in FIGS. 1 and 2 has a live ring 1 on which an x-ray source 2 and a radiation detector 3 are mounted. As shown in FIG. 1, the radiation detector 3 consists of a row of detector elements 3a, 3b . . . in front of which a collimator 4 is disposed. A fan-shaped x-ray beam 5, gated by a diaphragm 6, is incident on the radiation detector 3. The x-ray beam 5 penetrates a patient 7 on a support 8 disposed in an examination aperture 9. For portrayal of an image of a portion of a cross-section of the patient, the live ring 1 rotates around an axis 10, so that the patient 7 is transirradiated from different directions. A computer 11 constructs an image from the output signals of the detector elements 3a, 3b . . . and generates signals for a visual reproduction of the image on a display 12.

As shown in FIG. 1, the radiation detector 3 is significantly narrower than the patient support 8, i.e., subtends and angle, so that only a portion of a cross-section, or slice, of the patient 7 is visually portrayed. A measuring field 13 including the relevant patient cross-section is shown in FIG. 1, which is significantly smaller than the examination aperture 9. The size of the measuring field 13 is sufficient for locating calculi, because the position of the calculi-containing organ is known, and the position of this organ and the calculi contained therein will change position only slightly during treatment.

A shock wave generator 14 is also shown in FIGS. 1 and 2, aligned to the calculi to be disintegrated. For this purpose, the calculi must be positioned in the range of focus of the shock wave generator 14, which can be easily accomplished using the computer tomography apparatus as a locating device. The shock wave generator 14 may optionally contain an ultrasound locating system 22, as schematically indicated in FIGS. 3 and 4.

To generate an image which can be diagnostically interpreted with accuracy, the measuring unit, consisting of the x-ray source 2 and the radiation detector 3, must rotate around the axis 10 through at least an angle of 180°+l, where l is the fan angle of the x-ray beam 5. A plurality of radiation beams disposed side-by-side offset along the axis of rotation 10 (i.e, offset in the z-direction) emanating from a common focus 15 can be gated by the diaphragm 6 for portraying a plurality of slices. FIG. 2 shows only the radiation beam which visually portrays the region 16 of the patient 7; the other radiation beams respectively penetrate regions 17 and 18 and are respectively incident on detector rows 19 and 20 aligned to the focus 15, and disposed next to (i.e. offset in the Z-direction) the detector row formed by the detectors 3a, 3b....

The shock wave generator 14 can be permanently or detachably connected to the computer tomography apparatus, and is displaceable in the direction of a central propagation axis 21 for the shock waves, so that the region of focus of the shock wave generator 14 is adjustable relative to the calculus to be disintegrated. A possible combination of the computer tomography apparatus with the shock wave generator is shown in FIG. 3.

Figure 4:
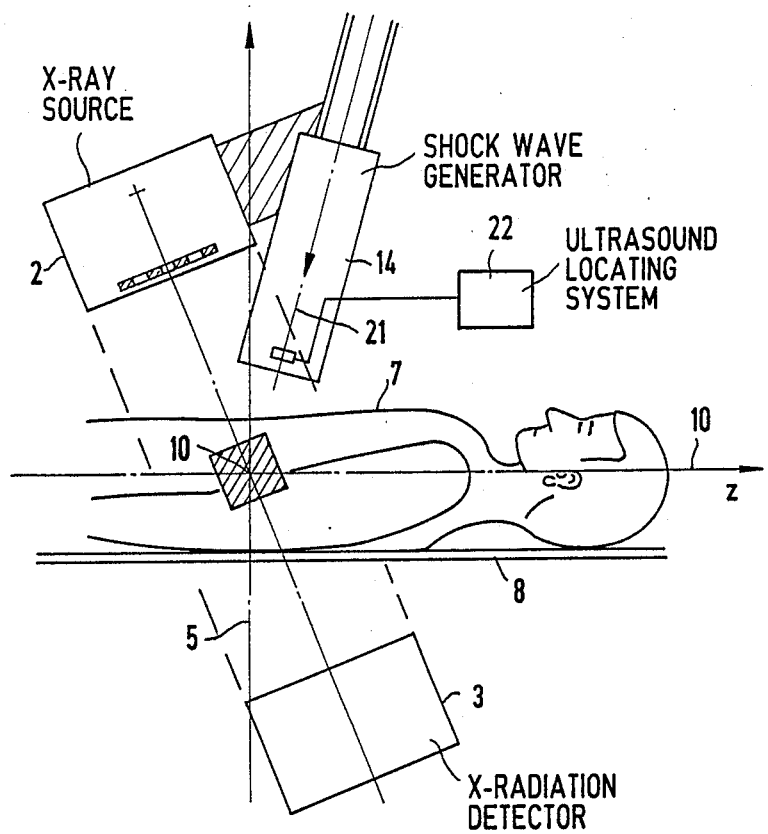

As can be seen in FIG. 3, the measuring unit and the shock wave generator 14 are arranged in a fixed, three-dimensional allocation relative to each other in the direction of the support 8, so that the shock wave 21 and the plane of the x-ray beam 5 have a spacing "a" from each other. For localization and for monitoring the lithotripsy treatment, the patient 7 is brought from the treatment position to the localization position, and may be returned to the treatment position, if needed, by longitudinal displacement of the patient support 8 along the path "a". This displacement can take place in freely selectable time segments during and following the treatment. The shock wave generator 14 need not proceed precisely vertically relative to the propagation direction of the x-ray beam 5, but can assume any angular position in a plane parallel to the x-ray beam 5, as shown in FIG. 1. The patient support 8 may be provided with recesses to permit coupling of the shock wave generator 14 to the patient from below.

As shown in FIG. 4, the shock wave 21 describes an angle relative to the plane of the x-ray beam 5 so as to roughly intersect the x-ray beam 5 at the axis 10, at which the focus of the shock wave generator 14 is also disposed. The region of intersection is thus above the patient support 8. In the embodiment of FIG. 4, displacement of the patient 7 for localization and monitoring, which is required in the embodiment of FIG. 3, is no longer necessary. The fan-shaped x-ray beam 5 can be tilted out of the vertical by a selected angle, and the shock wave axis 21 also describes an angle with the x-ray beam 5.

An example of the treatment of a patient using the computer tomography apparatus described above is as follows.

The position of the calculi to be treated is defined in two planes by conventional x-ray shadow images, which are produced with the support 8 and the patient thereon being displaced along the z-axis. The patient 7 is then displaced vertically and laterally on the support 8 so that the calculus comes to lie at the point of intersection between the x-ray beam 5 and the central axis 21 of the shock wave generator 14. The shock wave generator 14 is put in place, and may be more precisely positioned, if needed, by an ultrasound locating system integrated in the shock wave generator 14. If needed, another computer tomography exposure can be undertaken after this positioning in the embodiment of FIG. 4. As warranted, the movement and disintegration of the calculus are tracked during the treatment using the ultrasound system in the shock wave generator 14. If a re-positioning of the patient is advisable, or if the degree of disintegration of the calculus is to be determined, a computer tomography exposure is produced and the patient 7 is re-positioned, if necessary.

Although modifications and changes may be suggested by those skilled in the art it is the intention of the inventor to embody within the patent warranted hereon all changes and modifications as reasonably and properly come within the scope of his contribution to the art.

I claim as my invention:

1. A computer tomography apparatus for examining a patient comprising:

x-ray means for generating a fan-shaped x-ray beam adapted for transirradiating a portion of a transverse slice of a patient;

means for detecting x-radiation attenuated by said patient including a row of detector elements disposed to subtend an angle to receive said x-radiation from only said portion of said slice of said patient, said detector elements respectively generating output signals corresponding to the x-radiation incident thereon;

means for mounting said x-ray means and said means for detecting in a fixed relation and for rotating said x-ray means and said means for detecting around an axis extending through said portion of said slice of said patient; and means for constructing an image of only said portion of said slice of said patient from said output signals of said detectors.

2. A computer tomography apparatus as claimed in claim 1, further comprising:

means for gating said fan-shaped x-ray beam for generating a plurality of additional fan-shaped x-ray beams each offset in the direction of said axis and each irradiating a respective additional slice of said examination subject also offset in the direction of said axis; and a plurality of additional rows of detector elements respectively disposed to receive radiation attenuated by said examination subject from one of said additional fan-shaped x-ray beams, and each disposed to subtend an angle so as to receive x-radiation from only a portion of a respective additional slice.

3. A computer tomography apparatus as claimed in claim 1, further comprising:

a shock wave generator for extracorporeal lithotripsy adapted for disintegrating a calculus in said patient, said shock wave generator having an axis along which shock waves propagate; and means for mounting said shock wave generator in a fixed position relative to a plane containing said fan-shaped x-ray beam, said means for mounting allowing adjustment of said shock wave generator in a direction parallel to said axis of said shock wave generator.

4. A computer tomography apparatus as claimed in claim 3, wherein said shock wave generator includes an ultrasound locating system.

5. A computer tomography apparatus as claimed in claim 3, further comprising:

means for rigidly mounting said shock wave generator in a fixed position relative to said x-ray means and said means for detection.

6. A computer tomography apparatus as claimed in claim 5, wherein said means for rigidly mounting includes means for maintaining a predetermined distance between said plane containing said fan-shaped x-ray beam and said axis of said shock wave generator.

7. A computer tomography apparatus as claimed in claim 5, wherein said computer tomography apparatus further comprises a table adapted to support said patient, and wherein said means for rigidly mounting is a means for mounting said shock wave generator so that said axis of said shock wave generator intersects said plane containing said fan-shaped x-ray beam above said table.

8. A computer tomography apparatus for examining a patient comprising:
- a live ring being rotatable around an axis and surrounding said patient;
- x-ray means mounted on said live ring for generating a fan-shaped x-ray beam adapted for transirradiating a portion of a slice of a patient;
- means mounted on said live ring in fixed relation to said x-ray means for detecting x-radiation attenuated by said patient, said means for detecting including a row of detector elements disposed to subtend angle to receive said x-radiation from only said portion of said slice of said patient, said axis extending through said portion, and said detector elements respectively generating an output signal corresponding to the x-radiation incident thereon;
- means for generating shock waves to disintegrate a calculus in said portion of said slice of said patient, said means for generating shock waves being mounted in a fixed position relative to said live ring; and
- means for constructing an image of only said portion of said slice of said patient from said output signals of said detectors to locate said calculus.

* * * * *